United States Patent [19]

Diatschenko et al.

[11] Patent Number: 5,756,898
[45] Date of Patent: May 26, 1998

[54] PASSIVE ACOUSTIC METHOD OF MEASURING THE EFFECTIVE INTERNAL DIAMETER OF A PIPE CONTAINING FLOWING FLUIDS

[75] Inventors: Victor Diatschenko, Houston; James Raymond Stoy, Missouri City; Winthrop Kent Brown, Bellaire; Anna Nicole Ledoux, Sugar Land, all of Tex.

[73] Assignee: Texaco Inc., White Plains, N.Y.

[21] Appl. No.: 573,654

[22] Filed: Dec. 18, 1995

Related U.S. Application Data

[63] Continuation of Ser. No. 265,886, Jun. 27, 1994, abandoned.
[51] Int. Cl.[6] .................................................. G01N 29/04
[52] U.S. Cl. ........................... 73/592; 73/587; 73/40.5 A
[58] Field of Search .................... 73/587, 592, 40.5 A, 73/646, 648, 584, 861.37, 861.38, 638, 637

[56] References Cited

U.S. PATENT DOCUMENTS

| | | |
|---|---|---|
| 3,170,152 | 2/1965 | Long . |
| 3,906,780 | 9/1975 | Baldwin .................................. 73/194 |
| 4,013,905 | 3/1977 | Breneman et al. . |
| 4,448,062 | 5/1984 | Peterson et al. ........................ 73/587 |
| 4,609,994 | 9/1986 | Bassim et al. .......................... 73/587 |
| 4,909,091 | 3/1990 | Ellmann et al. ........................ 73/592 |
| 4,935,195 | 6/1990 | Palusamy et al. ...................... 73/592 |
| 5,333,501 | 8/1994 | Okada et al. ........................... 73/592 |

Primary Examiner—Hezron E. Williams
Assistant Examiner—Helen C. Kwok
Attorney, Agent, or Firm—Henry H. Gibson; William J. Beard

[57] ABSTRACT

Changes in the internal diameter of a fluid handling pipes are measured by measuring the vibrational characteristics by a non-invasive, passive acoustic technique. Deviations from the normal vibrational characteristics are sensed and used to determine changes of increase or decrease in the pipe's internal diameter.

2 Claims, 3 Drawing Sheets

PASSIVE ACOUSTIC METHOD OF MEASURING THE EFFECTIVE INTERNAL DIAMETER OF A PIPE CONTAINING FLOWING FLUIDS

This application is a continuation of application Ser. No. 08/265,886 filed Jun. 27, 1994, now abandoned.

BACKGROUND OF THE INVENTION

1. The Field of the Invention

The present invention pertains to a method and apparatus using passive acoustic techniques to determine changes in the internal diameter of a pipe and, in particular, where such reductions and/or increases in pipe diameter are due to scale buildup, hydrate formation, wax deposition, corrosion, erosion, etc.

2. The Prior Art

Many fluid conducting pipe systems suffer from the accumulation of solid or solid-like material on the internal wall of the pipe. These accumulations serve to decrease the effective internal diameter of the pipe. Scale, hydrates and paraffin accumulations are problems common to effectively decreasing the internal diameter of pipes in the transportation of oil field production. Corrosion and erosion are two common causes for an increase in the effective internal diameter of pipes.

Any changes in the internal diameter can cause various problems with respect to the continued operation of the piping system. An effective reduction in the internal diameter of the pipe causes the velocity of the flowing fluid to increase and results in an increase in the frictional pressure drop in the operating pipeline. The increased frictional pressure drop is accommodated by the piping system and its prime mover in either of two ways. First, the pipeline's operating pressure at the inlet is increased to deliver the desired quantity of fluid at the required outlet pressure. This necessitates the consumption of more energy than would be required by an unrestricted pipeline. Second, the quantity of fluid flowing through the pipeline is reduced because the pressure at the inlet to the pipeline is limited.

If an accumulation of non-flowing material on the inside wall of a pipeline is detected or suspected by the operator, a "pig" is often launched into the pipeline to dislodge and remove the accumulation before the efficiency of the pipeline is compromised. Many difficulties can arise in pipeline pigging operations, not the least of which is a stuck pig which effectively blocks the pipeline from further use.

Corrosion or erosion in fluid conducting pipelines causes a reduction in thickness of the pipe-wall material which, if not detected in a timely manner, can lead to pipeline leaks, ruptures or similar catastrophic events.

It is therefore desirable that a measurement system be available to operators of pipelines which system is capable of detecting any changes in the internal diameter of the pipe. Ideally, the measurement system would not only be able to detect the presence of an accumulation but to measure its thickness as well. These measurements are useful in the following ways. First, detecting the onset of an accumulation of non-flowing materials or an increase in the pipe internal diameter can alert the operator of the pipeline that preventive measures should be taken. For example, if chemicals are added to the flowing fluid to prevent corrosion or accumulations, the concentration of chemicals injected can be optimized through the use of a system which measures the inside diameter of the pipe. Second, if pipeline pigs are used periodically as a preventive measure, a system by which pipe effective internal diameter is measured would allow the operator to minimize unnecessary pigging operations. The pig would be run only when the measurements define the need. Third, a change in the effective internal diameter of the pipe may be indicative of changes in the flowing system that are not ordinarily detected until other problems occur. A method of detecting accumulations or erosion/corrosion would therefore serve as an "early warning" system and enable the operator to enact measures to prevent larger problems.

Historically, there are devices that perform some of these measurements and a few can operate in environments approaching extreme hostility. One such class of devices involves the use of ultrasonic techniques. These types of measurement systems can be intrusive or non-intrusive depending on the application. Changes in the flow velocity for a constant volume flow rate indicate the presence of a reduced pipe cross sectional area, and therefore the accumulation of non-flowing materials. The accumulation of non-flowing materials on the wall of the pipe are likely, however, to cause this system to become inoperative in that the detector would become coated causing the ultrasonic signal to be highly attenuated thereby reducing the sensitivity of the measurement.

Fluid velocities can be obtained using Doppler flow meters. These ultrasonic devices can be non-intrusive (externally mounted on the pipe) and protected from the environment. The idea behind these devices is that an ultrasonic signal is continuously transmitted into a pipe containing fluids where scattering occurs from suspended solids, air bubbles, discontinuities, or disturbances in the flowing stream. The scattered signal is detected and its frequency is compared to the transmitted frequency. The difference in these frequencies is proportional to the fluid's velocity. These measurements are considered most accurate when evaluating fluids with newtonian flow profiles and containing suspended particles or air bubbles.

Generally, the designs of existing flow characterization systems using nuclear, acoustic, or electromagnetic methods only address a few of the idealized capabilities and concentrate on measuring a restricted set of parameters while actively probing the medium of interest. These measurement systems can be intrusive or non-intrusive and some may require a side steam sample to obtain the required data.

Passive types of measurement techniques in pipes, specifically simple detection of acoustic emissions or "listening," are available but limited in scope and applications. For instance, acoustic emissions can be used to detect: slug flow and the presence of sand in multi-phase pipelines (see U.S. Pat. No. 5,148,405); leaks in natural gas pipelines (see U.S. Pat. No. 5,117,676); and steam quality when the acoustic emissions are obtained from a calibrated steam jet produced by an orifice (see U.S. Pat. No. 4,193,290). It does not appear that the prior art teaches the use of acoustic emissions as a passive and non-intrusive method for quantitative detection the internal diameter of a pipe.

SUMMARY OF THE INVENTION

The present invention utilized passive acoustic techniques to make an independent measurement of the internal diameter of a pipe regardless of the flow conditions within the pipe.

BRIEF DESCRIPTION OF THE DRAWINGS

The present invention will now be described, by way of example, with reference to the accompanying drawings in which.

DETAILED DESCRIPTION OF THE INVENTION

The present invention deals with the use of a non-invasive, passive acoustic vibration detector system which is capable of recording the vibrations from the outer surface of a pipe. The received signal is recorded and analyzed to determine the internal diameter of the pipe at the point where measurements were taken.

Figure 1:
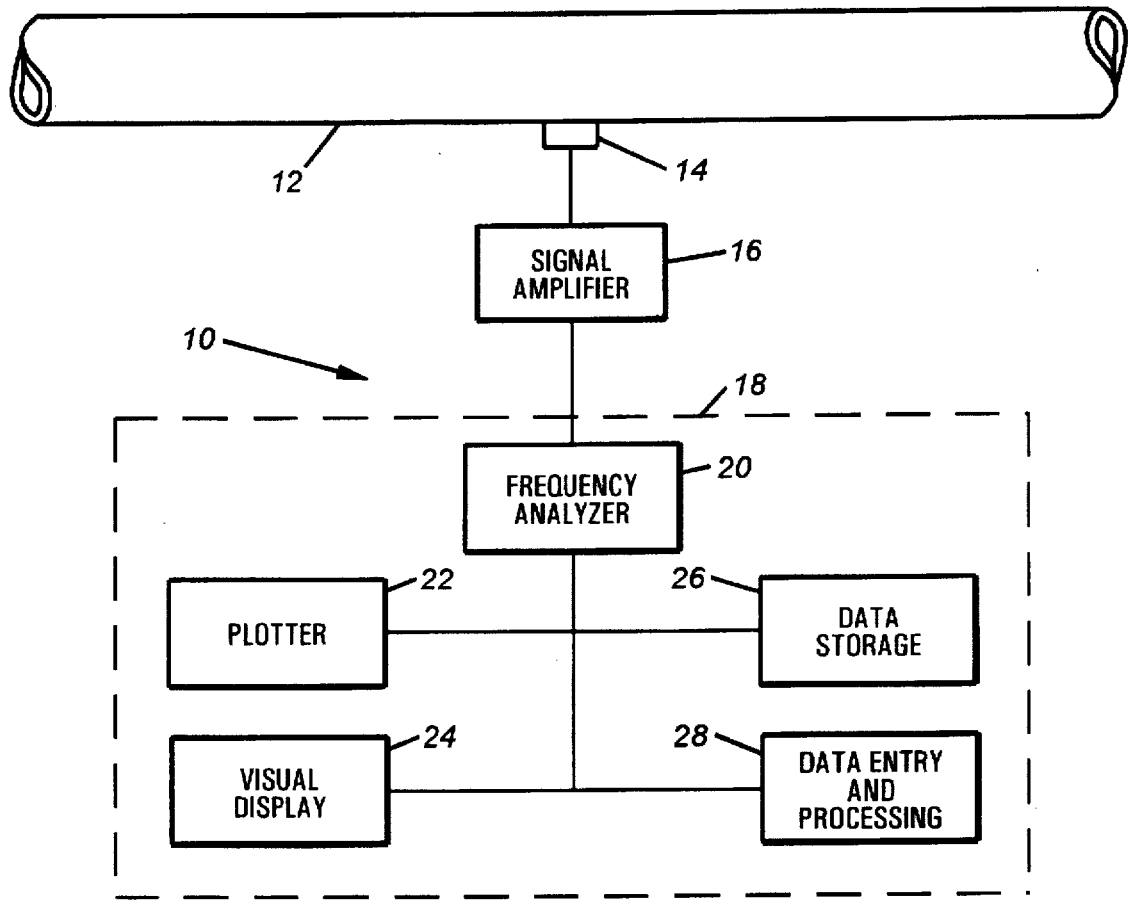
FIG. 1 is a diagrammatic representation of the present invention.

It is commonly known that fluids flowing through a pipe generate noise within the pipe. In principle, this naturally occurring phenomenon should be able to provide information about the fluids flowing in the pipe. FIG. 1 illustrates the apparatus 10 that has been used to quantitatively determine the inside diameter of a pipe 12 with a mixture of liquid and gas flowing through it. A vibration sensitive sensor means 14 sensitive in the range from 2.0 kHz to 30.0 kHz, such as an accelerometer, is placed in intimate contact with the pipe 12. The electrical signals from this sensor 14, if necessary, are fed into a pre-amplifier 16 for amplification and transmission to signal processing instrumentation 18. This instrumentation 18 would normally include: frequency analyzer means 20 capable of performing a Fast Fourier Transform (FFT) on the incoming time domain signals; frequency tracking means 22, such as a plotter; visual display means 24 for monitoring the frequency spectra; data storage means 26; and a means 28 for data entry and processing.

Several measurements were performed to identify the relevant parameters required to quantitatively describe the flow of gas-liquid mixtures. These experiments were conducted at low pressures and ambient temperatures using steel pipes of 0.5 inch, 0.75 inch and 1 inch in diameter and 8 feet in length. Air and water were used as gas-liquid mixtures. The flow rates in these measurements ranged from 0.25 GPM to 4 GPM (Gallons Per Minute) for water and 3 SCFM to 60 SCFM (Standard Cubic Feet per Minute) for air. These values correspond to total mass rates ranging from 2.3 lbm/min to 36 lbm/min.

Figure 2A:
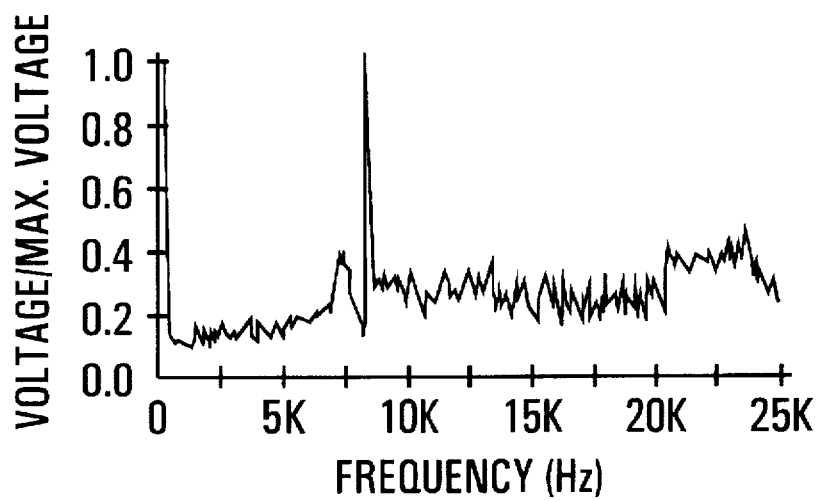
FIGS. 2A, 2B and 2C are frequency diagrams for one inch, three-quarter inch and half-inch pipe respectively.
Figure 2B:
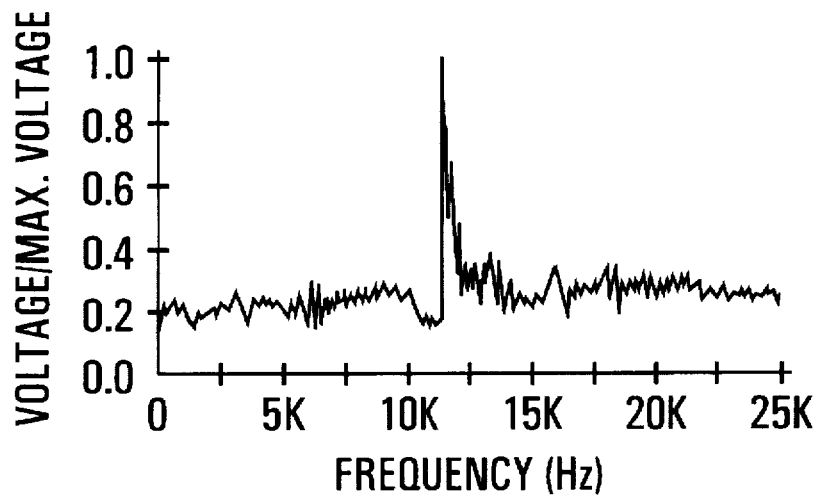
Figure 2C:
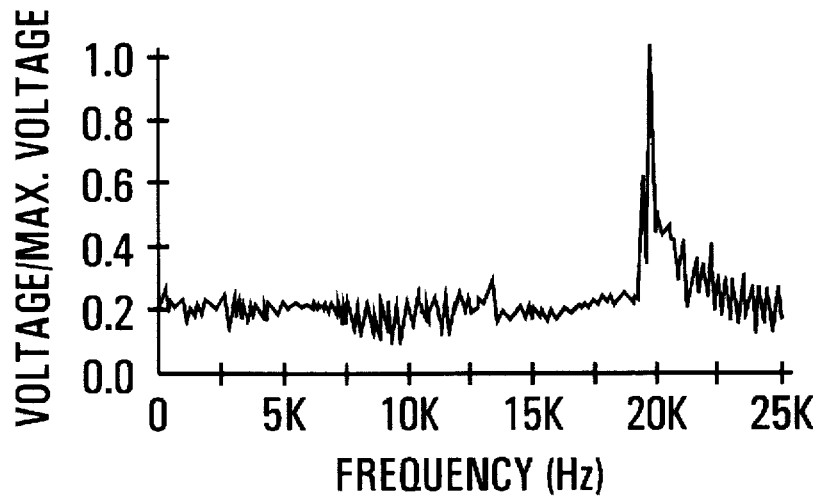
Figure 3:
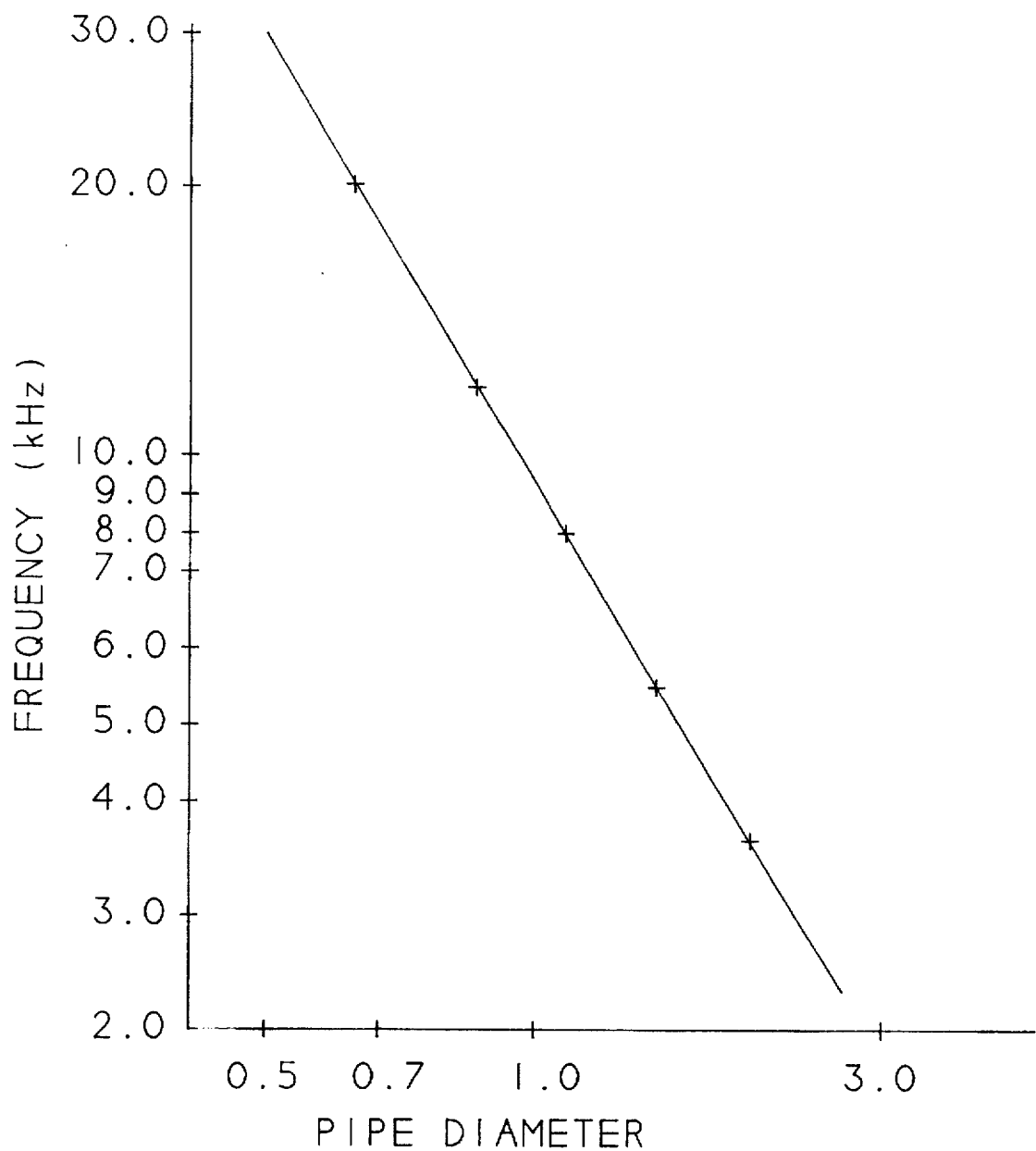
FIG. 3 is a graph showing the characteristic frequency dependence on pipe diameter.

The measurements have shown that the identification of the pipe's characteristic vibrational frequency variation is important to characterizing the fluid flow. The acoustic spectrum observed from 2.0 kHz to 30.0 kHz for a mixture of air and water in annular-mist flow in each of the three pipe sizes mentioned above is shown in FIG. 2. While the entire spectrum can be used to identify the flow regime, the same spectra also defines the pipe's characteristic vibrational frequency. That is, the most distinguishable single frequency common to all flow regimes. For the 1 inch in diameter pipe, the peak at 8.4 kHZ identifies the pipe's characteristic frequency. This high frequency suggests that the pipe's vibrations are primarily radial vibrational modes rather than transverse or longitudinal vibrational modes. These results also indicate that the characteristic frequency is strongly dependant on the pipe's internal diameter. This dependance has been measured in pipes ranging from 0.5 inches in diameter to 2 inches in diameter and is show in FIG. 3.

A change in the diameter of the inside of the pipe, whether decreased due to the accumulation of non-flowing material or increased due to corrosion or erosion, is detected by a shift in the characteristic frequency of the pipe. An increase in the internal diameter is manifest by a decrease in the characteristic frequency while a decrease in the internal diameter is manifest by an increase in the characteristic frequency.

Two aspects of this invention are unique. First, though the use of acoustic techniques is common in current measurement of pipe wall thickness and fluid velocity, all of the current techniques require that the pipe or fluid be acoustically stimulated by a means independent to the flowing system. This invention requires no such stimulation; it is entirely passive in that it requires only that the vibrations natural to the flowing system be detected and analyzed. Second, the measurement of the internal diameter of the pipe requires no prior knowledge of piping system operating conditions. Diameter measurements based on fluid velocity are based on a knowledge of fluid composition and volume rate flow as well as an assumption that the flow velocity is constant across the diameter of the pipe. Thus the present invention allows the measurement of internal diameter independent of flowing conditions.

The present invention may be subject to many modifications and changes which will occur to those skilled in the art without departing form the spirit or essential characteristics of the present invention. Therefor the foregoing description is intended in all respects as being illustrative and not restrictive of the scope of the invention as defined by the appended claims.

We claim:

1. A method for determining the effective internal diameter of a pipe using non-invasive passive acoustic techniques, comprising the steps of:

flowing fluid through a pipe and inducing vibration in said pipe;

providing at least one vibration sensor in intimate physical contact with said pipe and capable of detecting radial mode vibrations of said pipe in a frequency spectrum range from 2.0 kHz to 30.0 kHz;

determining a radial mode characteristic frequency and an amplitude of the characteristic frequency of vibration of said pipe in the frequency spectrum range from 2.0 kHz to 30.0 kHz;

tracking changes of said characteristic frequency and said amplitude; and determining from said changes of said characteristic frequency and said amplitude of said radial mode vibration attributable or a function of increasing as decreasing the internal diameter of said pipe.

2. The method of claim 1 and further including the step of:

determining from a predetermined inverse functional relationship between the radial mode characteristic frequency of said pipe taken as a function of effective pipe internal diameter, the effective internal diameter of said pipe.

* * * * *